(12) United States Patent
Smith

(10) Patent No.: US 6,461,308 B1
(45) Date of Patent: Oct. 8, 2002

(54) APPARATUS FOR DETECTING THE PRESENCE OF PATHOLOGY

(75) Inventor: Leslie R. Smith, Corfu, NY (US)

(73) Assignee: Probe Diagnostics, Inc., Batavia, NY (US)

( * ) Notice: Subject to any disclaimer, the term of this patent is extended or adjusted under 35 U.S.C. 154(b) by 0 days.

(21) Appl. No.: 09/804,839

(22) Filed: Mar. 13, 2001

(51) Int. Cl.[7] ................................................. A61B 5/00
(52) U.S. Cl. ..................................... 600/551; 600/547
(58) Field of Search ............................... 600/547, 551, 600/559

(56) References Cited

U.S. PATENT DOCUMENTS 4,224,949 A * 9/1980 Scott et al. .................. 600/551
4,498,481 A * 2/1985 Lemke ........................ 600/547
5,499,631 A * 3/1996 Weiland ...................... 600/547

* cited by examiner

*Primary Examiner*—Max Hindenburg
(74) *Attorney, Agent, or Firm*—Greenwald & Basch, LLC; Howard J. Greenwald

(57) ABSTRACT

A process of determining the presence of an abnormal condition within the body of a human female with a probe which contains a first conductive helical surface and a second conductive helical surface. In this process, the probe is abraded until its conductive helical surfaces are substantially free of oxidation products. Thereafter the probe is sterilized, the first helical surface is charged with a negative polarity, the second helical surface is charged with a positive polarity, and the probe is inserted into a human female's vagina to stimulate the flow of mucous. The resistance between the first and second helical surfaces is measured, and from this measurement is calculated the conductivity of the mucous within the female's vagina. This process is repeated several times over a period of time determine whether the mucous conductivity pattern of such period of time is within normal bounds.

17 Claims, 11 Drawing Sheets

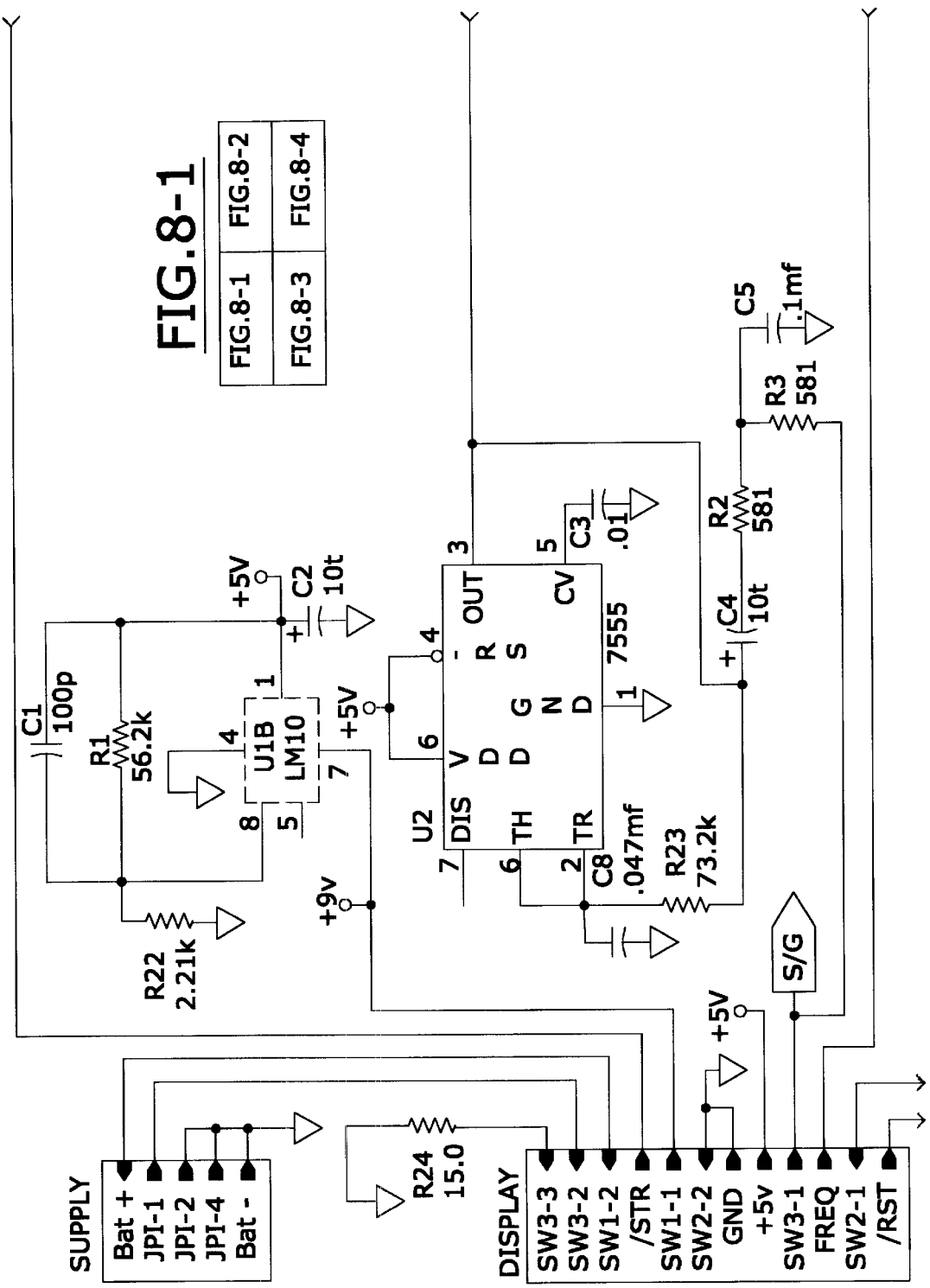

| FIG.8-1 | FIG.8-2 |
|---|---|
| FIG.8-3 | FIG.8-4 |

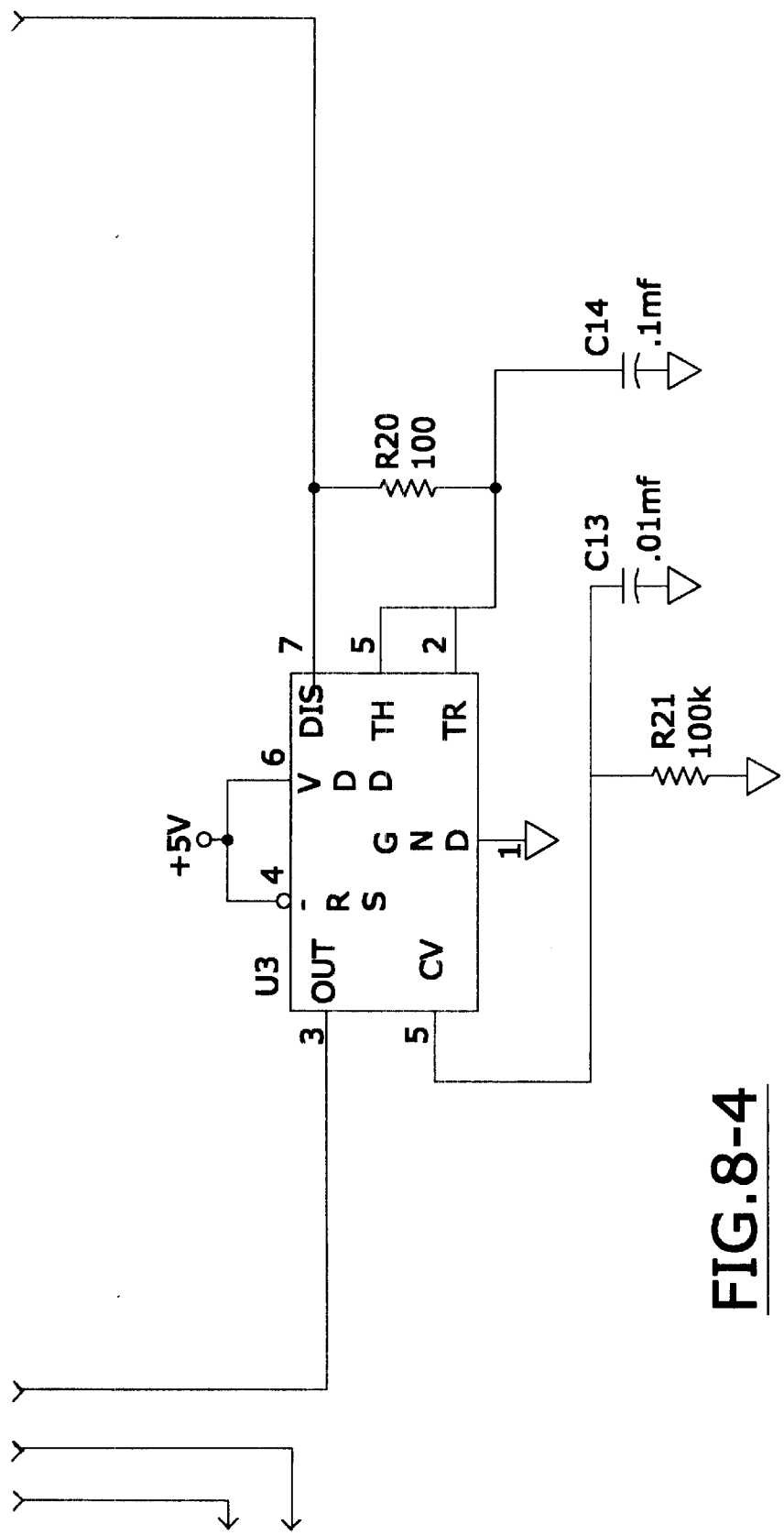

APPARATUS FOR DETECTING THE PRESENCE OF PATHOLOGY

FIELD OF THE INVENTION

A detector probe assembly for detecting the presence of pathological conditions in human beings. The probe is inserted into a human vagina; and, after measuring the electrical conductivity of the vaginal fluids, correlates these measurements with various conditions.

BACKGROUND OF THE INVENTION

Inexpensive and accurate means for determining various internal conditions within the human body are not available. It is an object of this invention to provide a relatively simple apparatus which can indicate the presence of a multiplicity of conditions within the human body.

SUMMARY OF THE INVENTION

In accordance with this invention, there is provided a detector probe assembly which contains a probe which senses the electrical conductivity of vaginal fluids by means of a multiplicity of metal-containing helices wrapped within a plastic matrix. The readings obtained by the detector are analyzed in a controller, which correlates a multiplicity of such readings with various body conditions.

BRIEF DESCRIPTION OF THE DRAWINGS

The invention will be described by reference to the specification and the enclosed drawings, in which like numerals refer to like elements, and in which:

FIGS. 8-1, 8-2, 8-3, and 8-4 collectively comprise a schematic of one preferred circuit used in the controller of the apparatus of FIG. 1;

DESCRIPTION OF THE PREFERRED EMBODIMENTS

Applicant has discovered that, with the process of this invention, a person can readily determine the presence or absence of a multiplicity of pathological conditions with expert medical assistance. Applicant's invention is premised upon a discovery that the conductivity of human vaginal fluid follows certain patterns over time.

Figure 1:
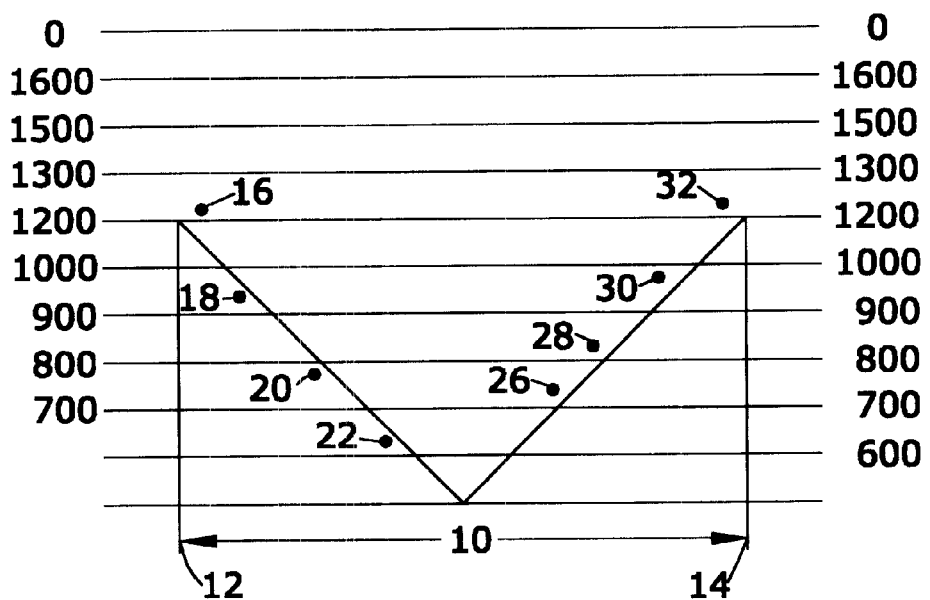
FIG. 1 is a graph of a series of readings of the conductivity of vaginal fluid within an animal taken over a period of 48 hours.

FIG. 1 is a graph of the conductivity of the vaginal fluid of a normal, healthy human female. The graph plots time 10 versus conductivity, in mhos. In the preferred embodiment illustrated in FIG. 1, the time at point 12 was deemed to be 0 hours, at the time at point 14 was deemed to be 28 days. A multiplicity of measurements were taken at times 16, 18, 20, 22, 24, 26, 28, 30, and 32 at substantially equal intervals during the 28 day period.

It is preferred that the measurement 16 be taken about one day after a woman's menstrual cycle has ceased as evidenced by the presence of bleeding. In general, at time 16, the conductivity reading will be at least about 1200 millimhos.

After measurement 16 has been taken, additional measurements may thereafter be taken to measure the decline in the conductivity readings. Although four such additional measurements have been shown in FIG. 1 (measurements 18, 20, 22, and 24), more such measurements or fewer such measurements may be taken. In general, after measurement 16 has been taken, it takes about twelve days for the conductivity of the vaginal fluids to decrease from a reading of at least about 1200 millimhos (see measurement 16) to a measurement of less than 600 millimhos (see measurement 24).

In general, the conductivity of the female's vaginal fluid reaches a low at about the twelfth day after menstruation. At about the fourteenth day after menstruation (see measurement 26), when the conductivity of the vaginal fluids is at least about 700 millimhos, the woman generally ovulates and is most likely to conceive upon having sexual intercourse. If sexual intercourse occurs at about the fourteenth day, the offspring is likely to be male.

The ovulation continues until about the sixteenth day (see measurement 28). If sexual intercourse occurs at about the sixteenth day, the offspring is likely to be male.

If sexual intercourse occurs prior to ovulation, by at least about 36 hours, the offspring is likely to be female. The female sperm are thought to be hardier but slower swimming than the male sperm and, because of their longer life spans, benefit from a "head start."

The pattern depicted in FIG. 1 is often disrupted when some pathology or abnormal condition occurs. Thus, by way of illustration, and referring to FIG. 2, the graph number 40, plotted over a period of nine days, shows conductivity readings ranging from about 1300 to in excess of 1600 millimhos. When a graph of this behavior is present, it typically indicates the presence of a excessive amount of air within the female's vagina, which can caused by several different conditions.

The graph number 42, also plotted over a period of nine days, shows conductivity readings ranging from about 1100 to about 1200 millimhos. When this condition is present, it often indicates the presence of estrus without ovulation. Estrus without ovulation is often caused by cysts within the female's reproductive tract. Cancerous conditions within the female's reproductive tract also can cause this condition to occur.

The graph number 44, also plotted over a period of nine days, shows conductivity readings ranging from about 1000 to about 600 millimhos. When this condition is present, cancer and/or some infectious disease may be present in the uterus of the female. In general, the lower the reading on graph 44, the more severe the pathological condition within the uterus.

In one embodiment of the process of the invention, the first reading 16 (see Figure is taken within one day after menstruation ceases), and thereafter subsequent readings are taken, It is preferred to take subsequent readings at substantially the same time of day as the first reading was taken, and it is preferred to have adjacent separated by about no more than 24 hours from each other.

Referring again to FIG. 1, although it depicts the normal female cycle, it should be understood that some females have cycles which occur over a shorter period of time than 14 days, and some females have cycles which occur over a longer period of time than 28 days. By making a repeated series of measurements with the process of this invention, a human female can determine her typical cycle, determine the best time(s) for her to conceive or not to conceive, and also determine whether any abnormal conditions are present in her system.

When an abnormal condition within a person's body is found to exist and is being treated, the apparatus and process of this invention will allow the patient to monitor and determine the effectiveness of the treatment.

Figure 2:
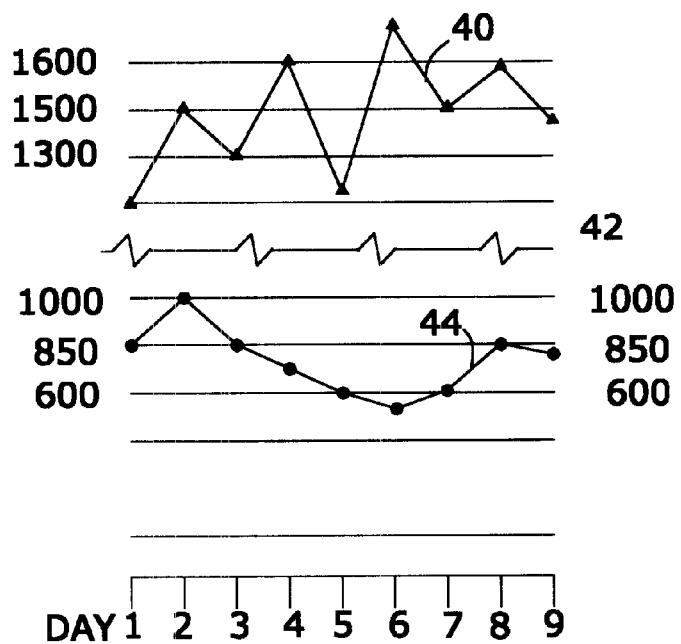
FIG. 2 is a graph is a graph of readings of vaginal fluid within an animal, taken over a period of nine days.

FIGS. 1 and 2 show how the conductivity of a woman's vaginal fluid varies with certain specified conditions. It should be understood, however, that there are many other conditions which causes the normal conductivity patterns to change. Such conditions include, e.g., pregnancy, follicular cysts, corpus luteum cysts, and the like.

Figure 3:
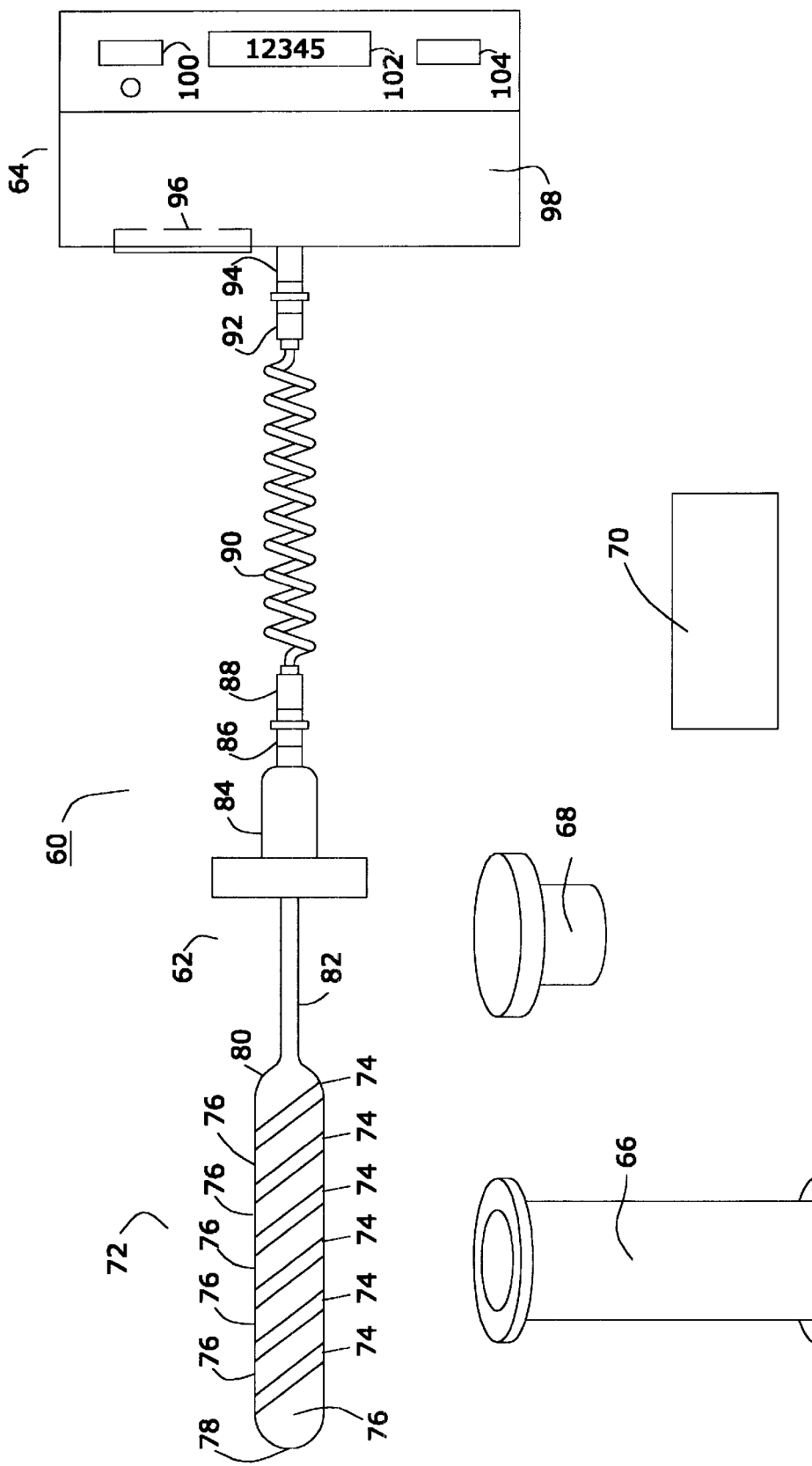
FIG. 3 is a schematic view of one preferred probe detector assembly of the invention.

FIG. 3 is a schematic representation of a detector probe assembly 60 comprising a detector probe 62 connected to a controller 64. In the preferred embodiment depicted, the assembly 60 also comprises a sterilization container 66, a cap 68 for container 66, and a scrub pad 70.

Referring again to FIG. 3, it will be seen that the detector probe 62 is comprised of sensor tip 72, which is inserted into the vagina of the female to be tested. The vaginal fluids contact helical metal-containing coils 74 which, preferably, are formed by a multiplicity of helices wrapped around each other. One such helical assembly may be used, two such helical assemblies may be used, etc. It is preferred to use two such helical assemblies.

The helical assemblies 74 are formed from a continuous, integral strand of metal-containing material shaped in the form of a helix. The metal-containing material is preferably a conductive metal-containing material. Suitable conductive metal-containing materials include, e.g., stainless steel, gold-plated plastic, nickel-plated plastic, copper-plated plastic, mixtures of gold/silver/copper-plated plastic, etc, elemental nickel, and the like.

In one embodiment, the metal-containing material is T316 stainless steel alloy material. In another embodiment, the metal-containing material is a plated strip of injection molded plastic in which the plating solution comprises gold ions, nickel ions, and copper ions.

In the preferred embodiment depicted in FIG. 3, the assemblies 74 are in the shape of a helix. The helical assemblies 74 are preferably embedded in a substantially non-conductive matrix 76. The non-conductive matrix 76 preferably is a non-conductive plastic matrix 76, such as, e.g., epoxy resin. In one embodiment, the material used in a "DP 270 black" epoxy sold by the Minnesota Mining and Manufacturing Company of St. Paul, Minn.

The helical assembly 74/conductive matrix 76 assembly has a substantially cylindrical shape with a substantially linear, smooth uninterrupted surface from its top 78 to its bottom 80. As will be apparent, this substantially continuous surface will not irritate the tissues of a woman's vagina.

In order to obtain such a smooth surface, once the helical assembly 74 is embedded within the matrix material 76, and the matrix material 76 has been cured, the entire assembly is machined to remove excess material and imperfections.

Connected to the assembly 74/matrix 76 device is a hollow rod 82 which, in one embodiment, is hollow stainless-steel tubing. Other materials which are corrosion-resistant also may be used such as, e.g., plastic material.

The rod 82 is connected to a hollow handle 84 which may be of any suitable shape and material. Connected to the end of handle 84 is a connector 86 which, in one preferred embodiment, is a twin BNC connector. Removably connected to twin BNC connector 86 is another twin BNC connector which, in turn, is connected to a shielded cable 90. As will be apparent to those skilled in the art, shielded cable 90 is impervious to radio frequency interference and, thus, is less likely to pass spurious signals to controller 64. In one embodiment, shielded cable 90 has an impedance of from about 50 to about 75 ohms and is often referred to as "AGW 50 to 75 microphone wire shielded." The cable 90, in the embodiment depicted, is in the form of coiled cable.

The distal end of cable 90 terminates in another twin BNC connector 92 which is removably connected to twin BNC connector 94. Twin BNC connector 94 is connected to controller 64.

The controller 64 is comprised of a receptacle (not shown) for receiving a battery, and a battery receptacle cover 96. The battery receptacle cover 96 is preferably disposed on the back side 98 of the controller 64.

Disposed on the front of controller 64 is a on-off button 100, a display 102, and a pause/run button 104.

After the probe detector 62 has been used, it may be disconnected from cable cord 90 and cleaned. To that end, a sterilization container 66 may be filled with a cleaning/sterilizing material. One may use conventional disinfectants such as, e.g., "NOLVASAN" disinfectant, which is manufactured and sold by the Upjohn Pharmaceutical Company. The use of such disinfectant is described, e.g., in U.S. Pat. Nos. 6,037,331, 5,886,554, 5,713,941, 5,098,417, and the like. The entire disclosure of each of these United States patents is hereby incorporated by reference into this specification.

It is preferred to use a mixture of water and disinfectant. In one embodiment, one may use a mixture comprised of one ounce of NOLVASAN and 30 ounces of water.

In one embodiment, instead of using the liquid disinfectant, or in addition thereto, one also may use disinfectant in gaseous form such as, e.g., chlorine dioxide, chlorine, formaldehyde, and the like.

The probe 72 may be scrubbed with pad 70 prior to or after the time it is immersed in the container 66 comprising the disinfectant mixture. It is preferred to scrub the probe 72 vigorously enough to remove oxidation products on the surface of the helical assembly 74.

After the probe 72 has been removed from the container 66, top 68 may be removably connected to container 66 to prevent the evaporation of disinfectant mixture contained therein.

Figure 4:
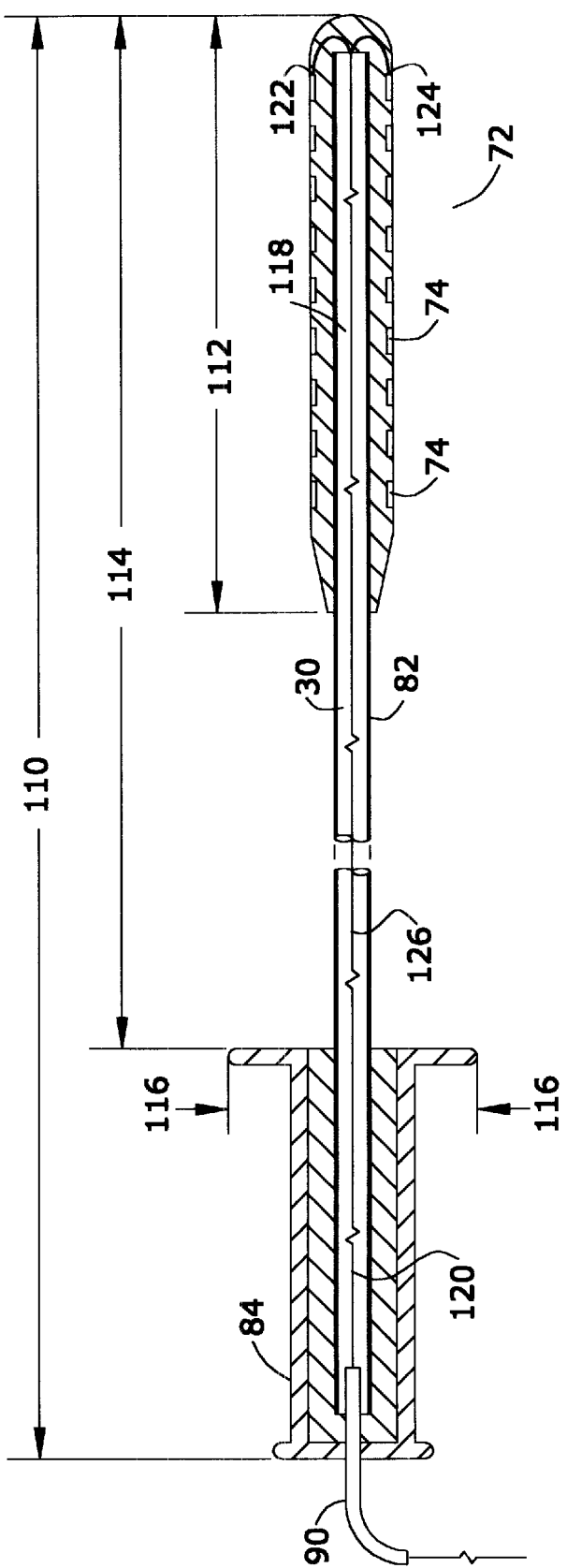
FIG. 4 is a broken apart sectional view of the detector probe used in the assembly of FIG. 3.

FIG. 4 is a broken apart sectional view of the detector probe used in the assembly of FIG. 3 from which unnecessary detail has been omitted for the sake of simplicity of representation. Referring to FIG. 4, and in the preferred embodiment depicted therein, assembly 60 has a length 110 of from about 9 to about 10 inches, sensor tip 72 has a length 112 of from about 1.5 to about 2.5 inches, length 114 is from about 5 to about 6 inches, and handle 84 has a diameter 116 of from about 1.0 to about 2 inches.

As will be apparent from FIG. 4, probe 72 has a hollow interior 118 in which is disposed conductive wires 120 connected to helical metal conductors 74. One such wire 120 is connected at junction 122, and another such wire 120 is connected at junction 124. Each of the helical wires 76 which are used are integral, electrically connected assemblies, so that the connections at points 122 and 124 reflect readings from each turn of each helix.

The rod 72 also comprises a hollow interior 126 through which wires 120 are disposed. In one embodiment, rod 82 has an outside diameter of from about 0.2 to about 0.4 inches, and the wires 120 are preferably 2–20 to 22 AWG stranded wires.

In the preferred embodiment depicted, after the wires 120 have been disposed within handle 84, such handle is filled with molten plastic in order to encapsulate the wires 120.

Figure 5:
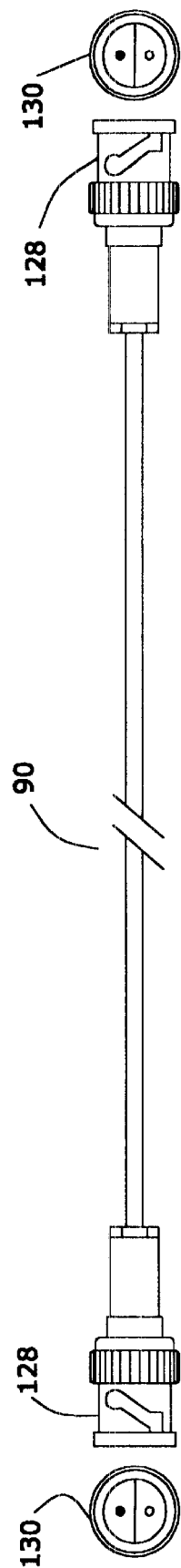
FIG. 5 is a partial schematic view of the assembly of FIG. 3, illustrating one preferred means of connecting the detector probe.

FIG. 5 is a partial schematic representation of cable 90, illustrating the use in such cable 90 of female twin BNC connectors 128 and male twin BNC connectors 130. In the embodiment depicted, cable 90 has a coiled length 132 of from about 22 to about 26 inches.

Figure 6:
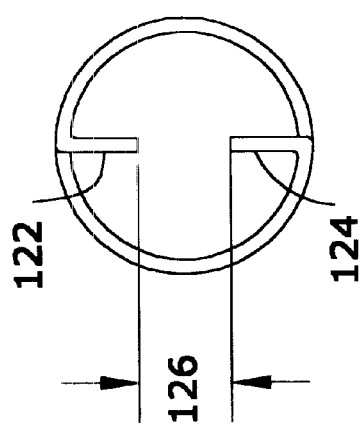
FIG. 6 is an end view of the helical coil assembly used in the assembly of FIG. 3.

FIG. 6 is an end view of the helical coil assembly used in the assembly of FIG. 3. Referring to FIG. 6, and in the preferred embodiment depicted therein, it will be seen that the distance 126 between the junctions 122 and 124 preferably is from about 0.1 to about 0.2 inches.

Figure 7:
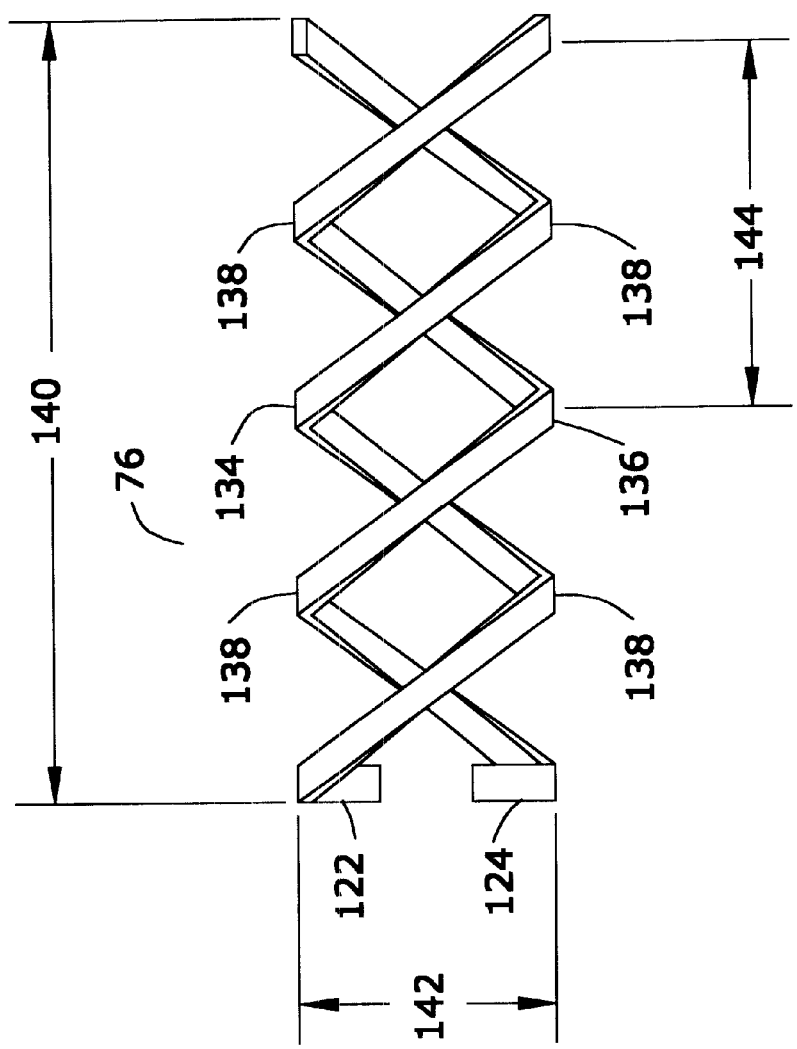
FIG. 7 is a top view of the helical coil assembly of FIG. 6.

FIG. 7 is a top view of the helical coil assembly of FIG. 6. In the preferred embodiment depicted in FIG. 7, it will be seen that helical assembly 76 is preferably comprised of two helices 134 and 136 interconnectedly wound so that their crowns 138 are substantially opposed to each other but out of phase with each other by from about 170 to about 190 degrees. Each of helices 134 and 136 is comprised of from about 1.5 to about 3 turns per linear inch of coil length 140. The diameter 142 of each of helices 134 and 136 is preferably from about 0.4 to about 0.5 inches. The pitch of each of helices 134 and 136, which is the distance 144 between adjacent turns of such helices, is from about 0.4 to about 0.6 inches.

Without wishing to be bound to any particular theory, applicant believes that the configuration of the helices 134 and 136 is critical in achieving the aims of this invention. In the process of invention, a minute electrical current is caused to flow through helices 136 and 138. One of said helices is preferably charged positively, the other of said helices is preferably charged negatively, and the current will flow from a negative point on the first helix to a positive point on the second helix. To the extent that vaginal mucous fluid is disposed between such first point and said second point, it will furnish some resistance and thus alter the rate of current flow. Consequently, with known values of positive and negative charges, the amount of resistance of the mucous fluid can be calculated. Thereafter, inasmuch as conductivity is the inverse of resistance, the conductivity of the mucous fluid may also be calculated. This conductivity can then be correlated in the manner described elsewhere in this specification with conditions such as, e.g., the temperature of the mucous membranes.

FIGS. 8-1, 8-2, 8-3, and 8-4 collectively comprise a schematic of one preferred circuit used in the controller 64 of the apparatus of FIG. 1. The circuit depicted in FIGS. 8-1, 8-2, 8-3, and 8-4 is especially useful when the probe assembly 60 of FIG. 3 is used to monitor the conditions of four-legged animals, such as horses and cows.

Figures 2, 8:
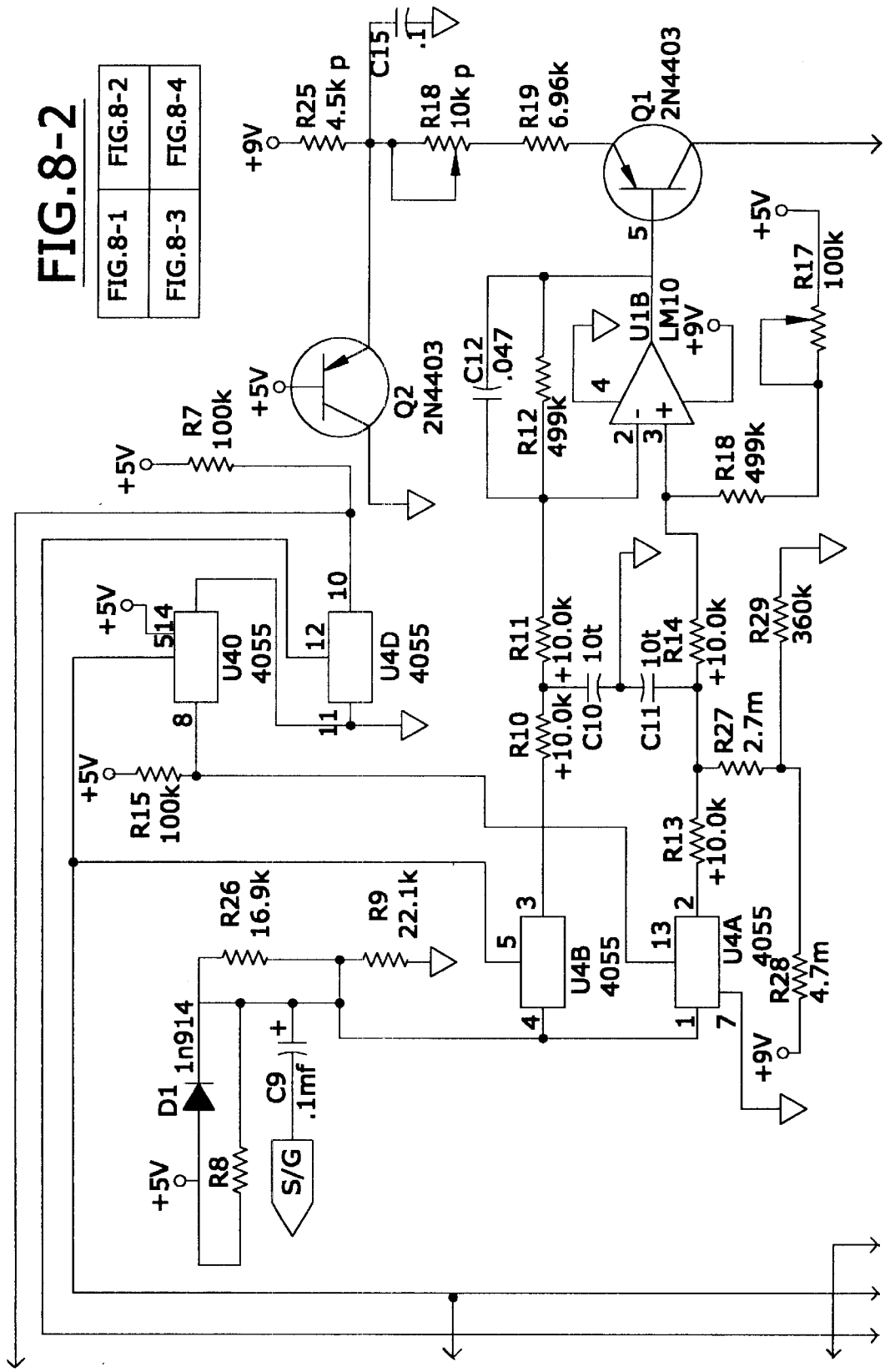
Figures 3, 8:
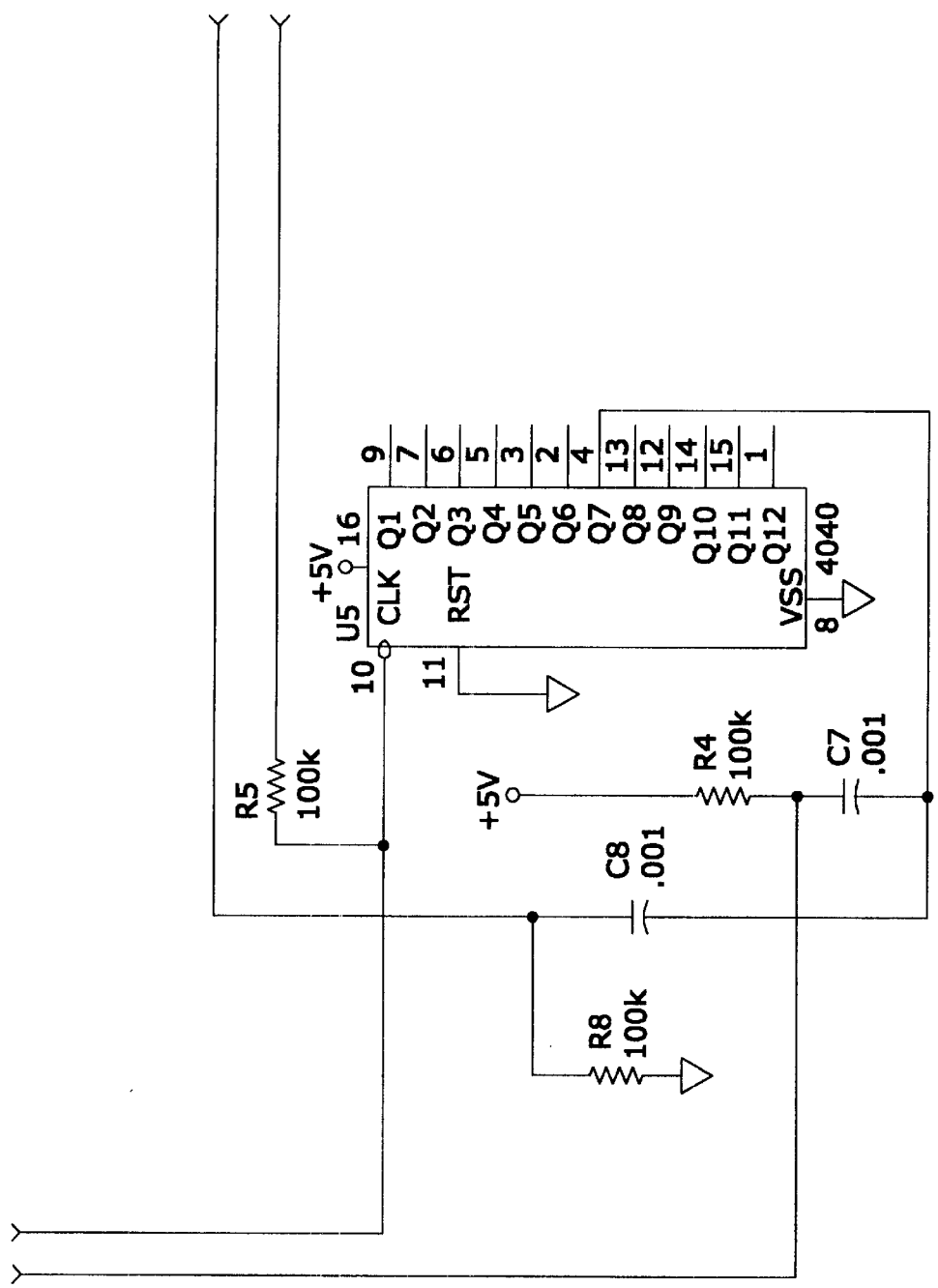
Figure 9:
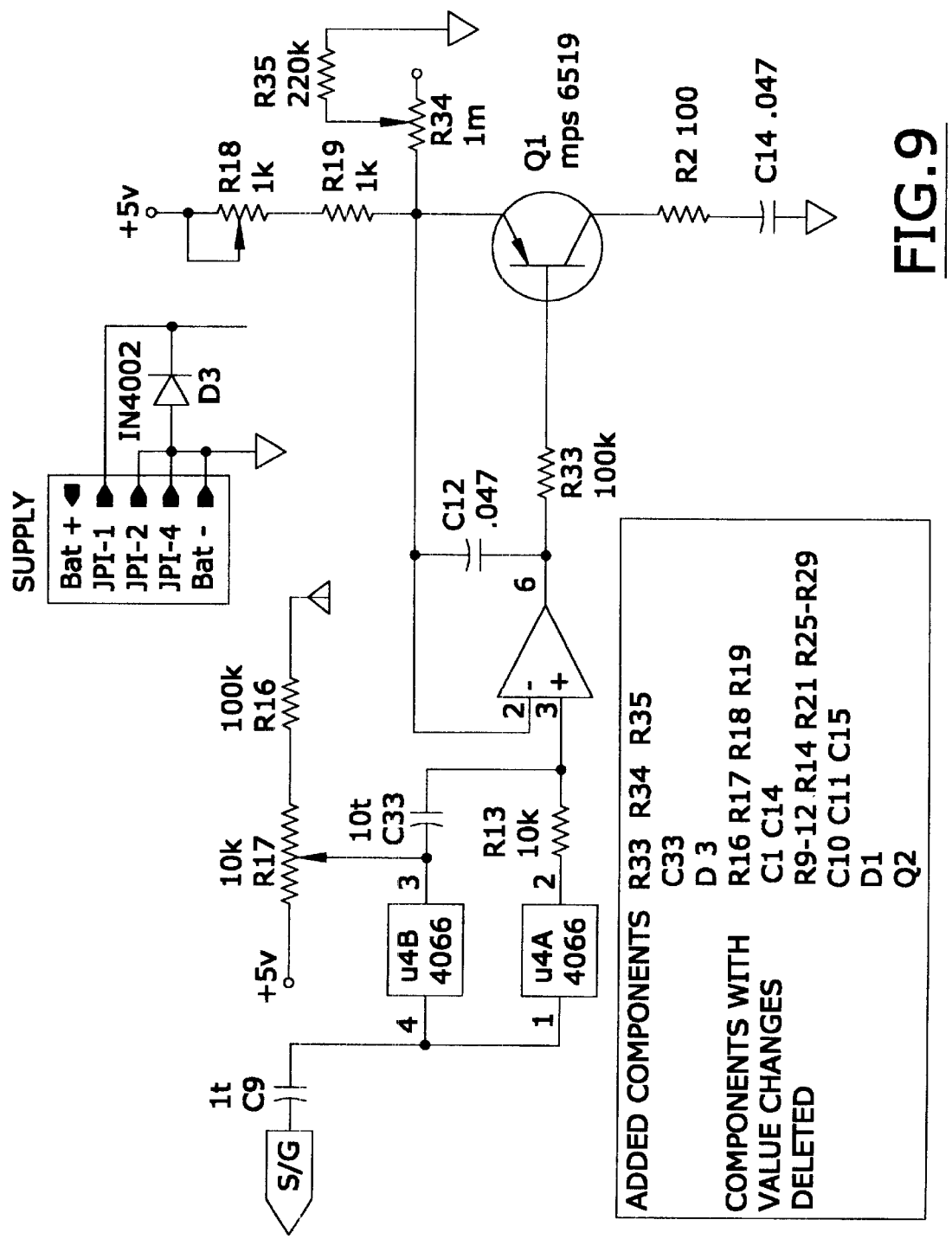
FIG. 9 is a schematic of another preferred circuit used in the controller of the apparatus of FIG. 1.

FIG. 9 is a schematic representations of the modifications which should be made to the circuit depicted in FIG. 8 to make such circuit useful in monitoring the conditions of two-legged animals, such as human females.

Figure 10:
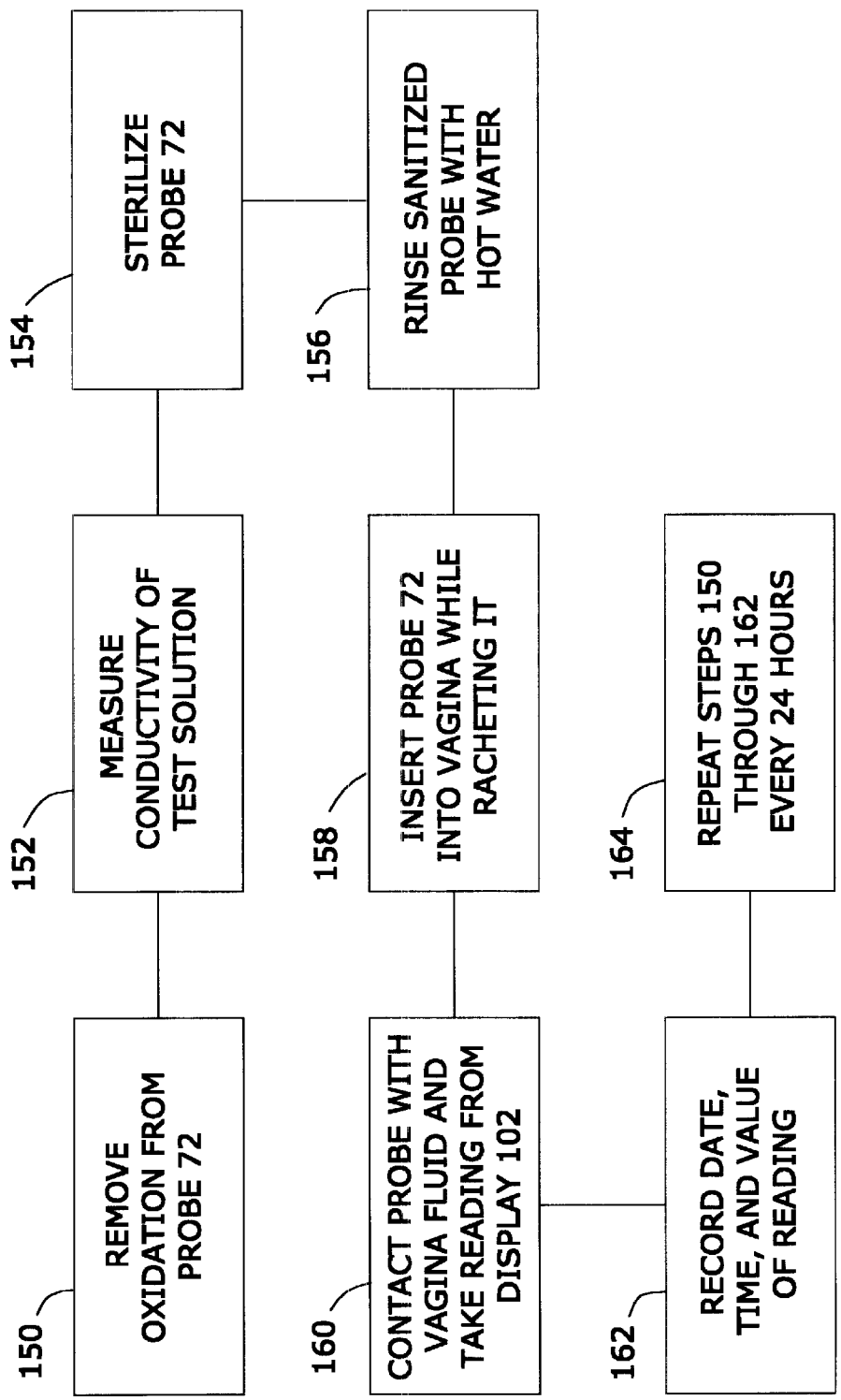
FIG. 10 is a flow diagram of one preferred process of the invention.

FIG. 10 is a flow diagram illustrating one preferred process of the invention.

In step 150 of the process, the probe 72 is scrubbed with scrub cloth 70 until any oxidized products on its surface have been removed. As will be apparent, oxidized products have different conductivities than their non-oxidized elemental metal counterparts.

In order to determine when sufficient scrubbing has occurred to remove the oxidation products, the conductivity of a specified test solution may be measured with the probe 72 in step 152. If the probe measurement does not reflect the specified conductivity of the test solution, scrubbing is continued until it does. One may use any suitable test solution such as, e.g., one gram of sodium chloride in 500 milliliters of distilled water.

In step 154, the probe 72 is sterilized. One may sterilize by the liquid disinfectant or gaseous disinfectant means described elsewhere in this specification.

In step 156 of the process, the sanitized probe 72 is then rinsed with hot water to remove any traces of disinfectant on it. Thereafter, in step 158, the probe 72 is inserted into a woman's vagina. The probe 72 is inserted into the vagina while rotating it in order to stimulate mucous flow from the vagina until it contacts the woman's cervical wall. Thereafter the probe 72 is retracted about one inch while rotating it in the opposite direction. Thereafter the probe 72 is again pushed towards the cervical wall while rotating in the first direction. This process is repeated for from about 15 to about 30 seconds to maximize the mucous flow from the vagina.

After from about 15 to about 30 seconds of maximizing the mucous flow from the vagina, the probe 72 is then returned to cervical wall and, with a firm pressure, laid flat on the floor of the vagina where it is allowed to rest while a reading is taken from the display 102 of the controller 64 in step 160. The pause/run button is preferably pressed after the reading is taken to lock it into the display 102. After the reading has been taken, steps 156 and 156 can be performed to sanitize the probe 72 which, after drying, can be put away for further use.

In step 162, a record is made of the date, time, and value of the reading taken in step 160. In step 164, steps 150 through 162 will preferably be repeated at least every 24 hours until a sufficient length of time has passed and a sufficient number of readings have been taken so that the user can construct a graph similar to that depicted in FIG. 1.

When this process has been repeated over several months, a "normal graph" for a particular user can be established. This "normal graph" will alert the user to the times when she is most likely to conceive. Additionally, if new readings indicate any substantial divergence from the "normal graph," the user will be alerted to the possibility that some abnormal condition might exist.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. A process of determining the presence of an abnormal condition within the body of a human female with a probe which contains a first conductive helical surface and a second conductive helical surface, comprising the steps of sequentially abrading said probe until each of said first conductive helical surface and said second conductive helical surface is substantially free of oxidation products, sterilizing said probe, charging said first helical surface with a negative polarity, charging said second helical surface with a positive polarity, inserting said probe into said human female's vagina, stimulating the flow of mucous from said human female's vagina with said probe, measuring the current flow between said first conductive helical surface and said second conductive helical surface, calculating the conductivity of said mucous, recording a reading of said conductivity of said mucous, and, thereafter, again sequentially abrading said probe until each of said first conductive helical surface and said second conductive helical surface is substantially free of oxidation products, sterilizing said probe, charging said first helical surface with a negative polarity, charging said second helical surface with a positive polarity, inserting said probe into said human female's vagina, stimulating the flow of mucous from said human female's vagina with said probe, measuring the current-flow between said first conductive helical surface and said second conductive helical surface, calculating the conductivity of said mucous, recording a reading of said conductivity of said mucous, and, thereafter, repeating this measurement process at least about three times over a period of at least about 4 days.

2. The process as recited in claim 1, wherein each of said first conductive helical surface and said second conductive helical surface is embedded within a substantially non-conductive matrix.

3. The process as recited in claim 2, wherein said substantially non-conductive matrix consists essentially of epoxy resin.

4. The process as recited in claim 1, wherein said probe is connected to a hollow rod.

5. The process as recited in claim 4, wherein said hollow rod is connected to a handle.

6. The process as recited in claim 5, wherein said handle is electrically connected to a controller.

7. The process as recited in claim 6, wherein said controller is comprised of a battery.

8. The process as recited in claim 1, wherein said probe is comprised of a hollow interior in which is disposed a first conductive wire and a second conductive wire.

9. The process as recited in claim 8, wherein said first conductive helical surface and said second conductive helical surface are entwined with each other such that said first conductive helical surface is out of phase with said second conductive helical surface by from about 170 to about 190 degrees.

10. The process as recited in claim 9, wherein each of said first helical surface and said second helical surface defines a first helix and a second helix, each of which contains from about 1.5 to about 3.0 turns per linear inch of said helix.

11. The process as recited in claim 10, wherein each of said first helix and said second helix has a diameter of from about 0.4 to about 0.5 inches.

12. The process as recited in claim 11, wherein each of said first helix and said second helix has a pitch of from about 0.4 to about 0.6 inches.

13. The process as recited in claim 1, further comprising the step of measuring the conductivity of a known test solution with said probe prior to the time said probe is abraded.

14. The process as recited in claim 13, further comprising the step of rinsing said probe with hot water after said probe has been sterilized.

15. The process as recited in claim 1, comprising the step of displaying said reading of said conductivity.

16. The process as recited in claim 15, wherein said reading of said conductivity is displayed on a display panel of a controller.

17. The process as recited in claim 16, further comprising the steps of temporarily freezing said display of said reading on said display panel of said controller.

* * * * *